(12) United States Patent
Duvert et al.

(10) Patent No.: US 11,065,184 B2
(45) Date of Patent: Jul. 20, 2021

(54) OIL-IN-WATER EMULSION FOR MAKING UP AND CARING FOR THE LIPS

(71) Applicant: LVMH RECHERCHE, Saint Jean de Braye (FR)

(72) Inventors: Amandine Duvert, Dampierre en Burly (FR); Marine Fabris, Saint Jean de Braye (FR); Aline Prevot, Fleury les Aubrais (FR); Aurore Durtschi, Saint Jean de Braye (FR); Chantal Kurfurst, Saint Jean de Braye (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 16/618,054

(22) PCT Filed: Dec. 17, 2018

(86) PCT No.: PCT/FR2018/053337
§ 371 (c)(1),
(2) Date: Nov. 27, 2019

(87) PCT Pub. No.: WO2019/122659
PCT Pub. Date: Jun. 27, 2019

(65) Prior Publication Data
US 2020/0100992 A1 Apr. 2, 2020

(30) Foreign Application Priority Data
Dec. 22, 2017 (FR) ...................... 1763099

(51) Int. Cl.
*A61K 8/06* (2006.01)
*A61K 8/39* (2006.01)
*A61K 8/81* (2006.01)
*A61K 8/86* (2006.01)
*A61Q 1/04* (2006.01)

(52) U.S. Cl.
CPC ............ *A61K 8/062* (2013.01); *A61K 8/39* (2013.01); *A61K 8/8129* (2013.01); *A61K 8/8158* (2013.01); *A61K 8/86* (2013.01); *A61Q 1/04* (2013.01); *A61K 2800/43* (2013.01); *A61K 2800/59* (2013.01); *A61K 2800/87* (2013.01)

(58) Field of Classification Search
CPC ........ A61K 8/062; A61K 8/39; A61K 8/8129; A61K 8/8158; A61K 8/86; A61Q 1/04
See application file for complete search history.

(56) References Cited

U.S. PATENT DOCUMENTS

| | | | |
|---|---|---|---|
| 2004/0191191 A1 | 9/2004 | Ehlis et al. | |
| 2007/0189989 A1* | 8/2007 | Cantwell | A61K 8/11 424/59 |
| 2007/0196295 A1* | 8/2007 | Cantwell | A61K 8/31 424/59 |
| 2009/0022680 A1 | 1/2009 | L'Alloret et al. | |
| 2013/0130959 A1* | 5/2013 | Li | A61K 8/585 510/119 |
| 2013/0280197 A1 | 10/2013 | Geffroy et al. | |
| 2013/0280198 A1 | 10/2013 | Cavazutti et al. | |
| 2016/0038402 A1* | 2/2016 | Lahousse | A61K 8/498 424/64 |
| 2017/0100314 A1* | 4/2017 | Diekhof | A61K 8/062 |

FOREIGN PATENT DOCUMENTS

| | | | |
|---|---|---|---|
| CA | 2796883 | 11/2011 | |
| EP | 1380288 | 1/2004 | |
| EP | 2018838 | 1/2009 | |
| FR | 2964868 | 3/2012 | |
| WO | WO-2012129722 A1 * | 10/2012 | ......... A61K 8/06 |

OTHER PUBLICATIONS

Database GNPD [Online] MINTEL; May 2014, "Fluid Stick Lipstick," XP002782677, Database accession No. 2401385 (6 pages).
International Search Report and Written Opinion issued for International Patent Application No. PCT/FR2018/053337, dated Feb. 26, 2019, 14 pages including English translation of Search Report.

* cited by examiner

*Primary Examiner* — Robert A Wax
*Assistant Examiner* — Olga V. Tcherkasskaya
(74) *Attorney, Agent, or Firm* — Hamre, Schumann, Mueller & Larson, P.C

(57) ABSTRACT

The invention relates to an oil-in-water emulsion for making up or caring for the lips. This emulsion contains a high proportion of glossy oils and is very fluid while remaining stable. This emulsion contains from 35% to 60% by weight of a mixture of oils, at least 25% by weight of water and from 0.01% to 20% of coloring material, everything being stabilized by the combination of a first polyethylene glycol ether of stearyl alcohol comprising from 2 to 5 oxyethylene units, a second polyethylene glycol ether of stearyl alcohol comprising from 15 to 25 oxyethylene units, and of a copolymer of acrylamido-2-methylpropane sulfonate and of hydroxyethyl acrylate.

8 Claims, 1 Drawing Sheet

OIL-IN-WATER EMULSION FOR MAKING UP AND CARING FOR THE LIPS

The invention relates to a product for making up and caring for the lips in the form of an oil-in-water emulsion. This emulsion contains the combination of two viscous oils in a high proportion, of pigments and of a system which disperses in the aqueous phase.

BACKGROUND OF THE INVENTION

Products for glossy lips are generally anhydrous and consist of high-viscosity glossy oils and of tacky hold polymer. The film obtained is then heavy and thick.

One means for obtaining a thinner film consists in emulsifying these oils in the internal phase of an oil-in-water emulsion. The film obtained can be thinner, on the one hand because the emulsion slides more easily over the lips than the anhydrous form at the time of application and, on the other hand, because the thickness of the film decreases by evaporation of the water on the lips after application.

However, there are numerous difficulties to be overcome in obtaining an oil-in-water emulsion containing glossy oils.

First of all, they are particularly difficult to stabilize when pigments are introduced therein in an amount sufficient to obtain a beautiful covering and tinted effect. When the stabilization is slight, the oil droplets can be detected visually by the consumer and give a negative perception of nonhomogeneity of the product. It is then necessary to package it in an opaque bottle. In point of fact, the presentation of a liquid product for making up the lips in a transparent bottle is greatly appreciated by consumers, who are thus in a position to immediately perceive the color which they are looking for, and it is desirable for the color perceived through the transparent bottle to be an accurate depiction of the color of the film of product deposited on the lips.

Subsequently, the oils of the internal phase of an oil-in-water emulsion generally develop a film of low gloss after deposition of the product on the lips, without it being possible to explain why.

Finally, consumers value lipsticks which provide a feeling of comfort and do not dry out the lips and thus maintain the initial level of hydration of the lips. However, they value more the products simultaneously contributing makeup and care of the lips, the care mainly targeting the rehydration of the lips.

One solution provided for retaining good gloss of the makeup and strong colors has consisted in introducing, into an oil-in-water emulsion, alkylcelluloses in dispersion in the water. Admittedly, the film left on the lips after the application of this type of product is glossy but the emulsion is not fine enough to be presented in a transparent packaging. Moreover, it is difficult to produce a makeup which is uniform in color and in thickness and to obtain a distinct outline of the lips during the application of the product. Finally, this type of product cannot act as care product which rehydrates the lips. An example of one of these formulations is described in the application FR 2 964 868.

SUMMARY OF THE INVENTION

The need consequently remains to provide a liquid product for making up the lips as an oil-in-water emulsion of homogeneous appearance in a transparent packaging, forming a thin, very glossy and very uniform film on the lips, the outlines of which are distinct. The need also remains to provide a product intended both for making up and caring for the lips and which has a strong moisturizing power.

Figure 1:
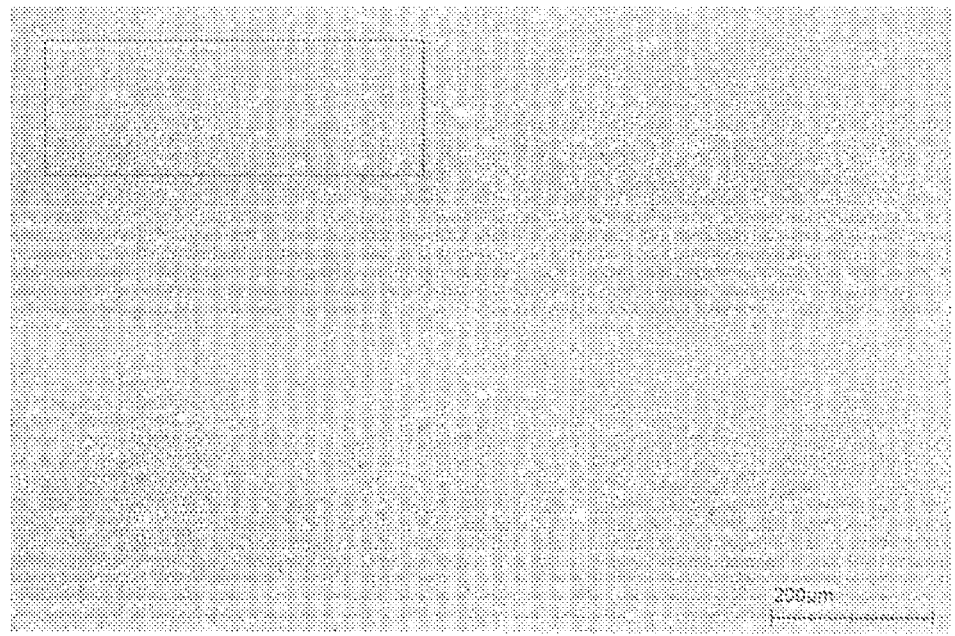
FIGS. 1 and 2 are micrograph images of emulsions as discussed in the examples below.

The composition of the present invention has made it possible to achieve these objectives.

DETAILED DESCRIPTION OF THE INVENTION

According to a first aspect of the invention, the invention relates to a liquid product for making up the lips as an oil-in-water emulsion comprising:

from 25% to 45% of a mixture of water and of at least one polyol, from 35% to 60% by weight, preferably from 40% to 50% by weight and more preferably from 45% to 50% by weight of a mixture of oils each having a refractive index of greater than or equal to 1.460 at a temperature ranging from 20° C. to 25° C., from 0.01% to 20% by weight of a coloring material, the percentages being expressed with respect to the weight of the emulsion, characterized in that it comprises a first ether of stearyl alcohol and of a polyethylene glycol comprising from 2 to 5 oxyethylene units, a second ether of stearyl alcohol and of a polyethylene glycol comprising from 15 to 25 oxyethylene units, and a copolymer of acrylamido-2-methylpropanesulfonate and of hydroxyethylacrylate.

The term "coloring material" is understood to mean a compound or a mixture of compounds chosen from pigments and dyes.

The mixture of the first ether, of the second ether and of the copolymer can perform the function of stabilizing mixture and advantageously makes it possible to emulsify from 35% to 60% of glossy fatty phase, to stabilize a lipophilic pigment dispersion and to stabilize the emulsion. The right stabilization of the emulsion makes possible the coalescence of the droplets of the fatty phase during the evaporation of the water on the lips to reveal the gloss thereof, while leaving no gelled masses on the lips after the drying of the film.

It is very surprising to obtain a pigmented emulsion, both fluid and stable, containing up to 50% by weight of internal phase, providing a twofold performance of caring for and making up the lips. Such a level of gloss for such a thin deposit of product on the lips had never been obtained previously.

Moreover, the invention describes a liquid product for making of the lips as an oil-in-water emulsion comprising:

from 25% to 45% by weight, for example from 30% to 40% by weight, of an aqueous phase comprising water and at least one polyol, from 0.01% to 20% by weight of a coloring material, from 1% to 4% by weight of at least two nonionic surface-active compounds, characterized in that it additionally contains an acrylamido-2-methylpropanesulfonate copolymer, and from 35% to 60% by weight of oils, including from 15% to 25% by weight of a mixture of methyl hydrogenated rosinate and of hydrogenated polycyclopentadiene, the percentages being expressed with respect to the weight of the product.

The emulsion of the invention makes it possible to obtain a makeup result of high gloss, light on the lips, without being tacky. This emulsion contains a high content of oils nevertheless deemed to be tacky and viscous by a person skilled in the art of cosmetics, and also a specific stabilizing system containing two surfactants and a polymer.

It is very surprising to be able to incorporate and stabilize such a high proportion of viscous oils in the internal phase of an oil-in-water emulsion, while retaining its stability and while revealing the gloss of the oils in the deposit left on the lips after application of the product and evaporation of the water. Without being committed to any theory, the inventors believe that the combination of ingredients used has made it possible to find a very precise balance between the stabilization of the oil droplets in the emulsion during the storage of the product, and the ability of these droplets to coalesce during the evaporation of the water in the product film which has been deposited on the lips. These two properties are a priori incompatible insofar as, the more the droplets are stabilized, the more difficult should be their coalescence. This unexpected property of the emulsion of the present invention thus makes it possible to emulsify glossy oils which are supposed to be difficult to emulsify in a stable fashion and to obtain, on the lips, a continuous film of oils, the uniform and smoothed surface state of which makes it possible to retain the intrinsic gloss of the starting materials and to obtain a lacquered effect.

This is why, although the oils participating in the composition of the emulsion are known independently of one another in the field of the formulation of anhydrous glossy products for lips, and although the stabilizing agents introduced into the emulsion of the invention have already been used to stabilize oil-in-water emulsions not containing glossy oils but very light oils which are easy to emulsify, the effect of the combination of these starting materials could not under any circumstances be foreseeable, this being all the more the case as the performance qualities of gloss and of hydration of the emulsified liquid lipstick of the invention have never been achieved to date.

Furthermore, the solutions which have been provided in the prior art for improving the gloss of a lipstick as oil-in-water emulsion do not rest on the structuring of the internal phase of the emulsion but on the use of film-forming polymers in the aqueous phase. The invention thus provides a very different formulation route for achieving objectives of higher gloss and of higher hydration.

The stability of the emulsion of the invention makes it possible to package it in transparent bottles, which renders the product much more attractive: this makes it possible in particular for the user to clearly visualize the color.

Other aspects of invention relate to i) a method for making up or caring for the lips which consists in applying, to the lips, one of the emulsions described above, ii) a process for the manufacture of one of the emulsions described above and iii) a transparent bottle having an applicator containing one of the emulsions described above.

In the continuation of the text, the percentages are expressed by weight with respect to the weight of the emulsion of the invention, unless explicitly mentioned otherwise.

In the present patent application, the expression "from . . . to . . . " is aimed at comprising the lower and upper limits of the range of values, while the expression "between . . . and . . . " excludes the limits of the range of values. The disclosure of a range of values excluding its limits has the value of the disclosure of the equivalent range of values including the limits, and vice versa.

The oils participating in the composition of the emulsion of the invention preferably represent from 35% to 60% by weight, more preferably from 40% to 50% by weight and more preferentially from 45% to 50% by weight. These oils are described by a person skilled in the art as heavy, viscous or glossy oils as the case may be.

These oils can, for example, have a refractive index, measured at a temperature ranging from 20° C. to 25° C., which is greater than or equal to 1.460 and preferably ranging from 1.460 to 1.580.

The refractive index of the oil can be measured by any method known to a person skilled in the art of cosmetics.

One method which makes it possible to measure the refractive index of an oil uses a refractometer from Anton Paar, model Abbemat® 300/500. The measurement temperature is adjusted to 20° C. or 25° C. A milliliter of the oil for which it is desired to measure the refractive index is deposited with the pipette on the clean prism and the measurement is carried out automatically by the apparatus.

A person skilled in the art of cosmetics may also refer to the technical data provided by the manufacturer of the oil.

Examples of such oils are phenylpropyl dimethylsiloxysilicate sold under the tradmark Silshine® 151 (n=1.509), POLYGLYCERYL-10 NONAISOSTEARATE sold under the trademark Sface® IS 1009 P (n=1.492), polybutene sold under the trademark Polybutene® M 2000 (n=1.492), TRIMETHYL PENTAPHENYL TRISILOXANE sold under the trademark DC PH® 1555 (n=1.579), 1,2,4-BENZENETRICARBOXYLIC ACID, BRANCHED TRIDECYL ISODECYL ESTERS sold under the trademark Liponate® TD™ (n=1.483), dilinoleyl dilinoleate sold under the trademark Lusplan® DD DA7 (n=1.482), the copolymer of polyglyceryl-2 isostearate and of dilinoleate dimer sold under the trademark Hailuscent® ISDA (n=1.476), DIPHENYL DIMETHICONE sold under the trademark KF® 54 HV (n=1.495-1.505) and TRIMETHYLOLPROPANE TRIISOSTEARATE sold under the trademark Salacos® 6318 V (n=1.466). In this paragraph, the refractive indices were measured according to the method described above at a temperature of 20° C.

The oil can also be chosen from diisostearyl malate, octyldodecanol, polybutenes, vinylpyrrolidone copolymers, hydrogenated polyisobutenes, polydecenes, poylglycerol-2 triisostearate, tridecyl trimellitate, ditrimethylolpropane isostearate/sebacate, dipentaerythrityl tri(polyhydroxystearate), dipentaerythrityl pentaisostearate, pentaerythrityl tetraisostearate, poylglycerol-2 tetraisostearate and castor oil. The refractive index of these oils is included among the technical characteristics provided by the manufacturer.

It is preferable to use, as glossy oil, a hydrogenated rosin ester, a hydrogenated polycyclopentadiene, a hydrogenated polyisobutene or one of the mixtures of these three oils, in particular a mixture of hydrogenated rosin ester and of hydrogenated polycyclopentadiene, or a mixture of hydrogenated rosin ester, of hydrogenated polycyclopentadiene and of hydrogenated polyisobutene.

Rosin (also known as rosinic acid) is an aromatic acid comprising a glucopyranoside unit. It is extracted from colophony, which is obtained after distillation and drying of an exudate harvested from coniferous trees, such as pines. The rosin ester is preferably METHYL HYDROGENATED ROSINATE (INCI name), such as that sold under the trademark Floralyn® by Laserson. The rosin ester can represent between 10% and 15% by weight. Its refractive index is equal to 1.515.

The hydrogenated polycyclopentadiene is, for example, introduced into the emulsion at a content ranging from 2% to 5% by weight, in particular as a mixture with another oil. Such a mixture can correspond to the commercial product sold under the trademark Kogoguard® 5400 CCT manufactured by Kobo. Its refractive index at 20° C. can be 1.503 and its viscosity, measured at 25° C., can be 2849 cPs.

Finally, the hydrogenated polyisobutene can be that sold under the trademark Parleam® HV (n=1.497) from NOF Corporation and be present at a content of 6% to 10% by weight.

The emulsion can contain oils other than the oils described above but preferably in an amount ranging from 0% to 15%, preferably of less than 10%. These oils can participate in the composition of the starting materials used in the manufacture of the emulsion. They can also act as means for dispersion of the pigments used in the coloring of the lips. A caprylic/capric triglyceride corresponds to one of these oils.

In a specific embodiment, the emulsion comprises the mixture of a first ether of stearyl alcohol and of a polyethylene glycol comprising from 2 to 5 oxyethylene units, of a second ether of stearyl alcohol and of a polyethylene glycol comprising from 15 to 25 oxyethylene units, and of an acrylamido-2-methylpropanesulfonate copolymer.

The first ether can have the INCI name STEARETH-2 or the one sold under the trademark Brij™ S2, and the second ether the INCI name STEARETH-21 or the one sold under the trademark Brij™ S721.

The acrylamido-2-methylpropanesulfonate copolymer is, for example, a copolymer of acrylamido-2-methylpropanesulfonate and of hydroxyethyl acrylate and can have the INCI name HYDROXYETHYL ACRYLATE/SODIUM ACRYLOYLDIMETHYL TAURATE COPOLYMER. It preferably represents from 0.2% to 1.0% by weight, for example from 0.6% to 0.9% by weight, of the weight of the emulsion. In a process for the preparation of the emulsion of the invention, the copolymer can be added to the other ingredients of the emulsion after having been predispersed in water. A ready-for-use predispersion of the copolymer is sold under the trademark SIMULGEL® NS by SEPPIC.

The emulsion of the invention can contain other surface-active compounds or coemulsifying agents, such as myreth-3 myristate (for example of the one sold under the trademark Lanol® 14 M), polysorbate 60 and sorbitan isostearate. These emulsifying agents can be used in particular to prepare a predisposition of the copolymer and to facilitate its incorporation in the emulsion.

The invention also describes an emulsion of the invention containing a mixture of at least one polymer present in the aqueous phase and of at least two nonionic surfactants, including a nonionic surfactant with an HLB of less than 8 and a nonionic surfactant with an HLB of greater than 8. This mixture can advantageously stabilize the dispersion of the oils and of the pigments.

The emulsion of the invention preferably comprises less than 0.2% by weight, preferably less than 0.15% by weight, of one of the compounds mentioned in the following list: hydroxyethylcellulose (such as those sold under the trademark Natrosol® range), crosslinked polyacrylates (such as the products of the INCI name POLYACRYLATE CROSSPOLYMER-6), xanthan gums (for example the gums sold under the trademark Rhodicare® XC and Rhodicare® T), carrageenans, hydroxymethylcellulloses, ethylcelluloses in dispersion, pullulan, agar, a polysaccharide produced by the bacterium Alcaligenes (for example the product sold under the trademark Alcasealan®) or polyurethane gels (sold under the trademark AdekaNol® range in particular).

The emulsion of the invention is advantageously devoid of one of the abovementioned gelling agents.

This is because it has been demonstrated that emulsions containing these compounds are not stable: a phase separation of the oils and of the water, the sedimentation of solid particles, an excessively fluid consistency of the product and/or the formation of product masses on the lips, once the product is deposited, is (are) observed.

The emulsion can contain from 25% to 45% by weight, for example from 30% to 40% by weight, of water.

Besides water, the aqueous phase of the emulsion can contain the copolymer of acrylamido-2-methylpropanesulfonate and of hydroxyethyl acrylate described above, pH adjusters (such as, for example, a citrate and/or citric acid), ethanol, at least one polyol, such as glycerol or butylene glycol, and sweeteners, such as stevioside sold under the trademark REBATEN®.

Thus, the emulsion of the invention can comprise from 3% to 15% by weight of polyol(s), in particular from 5% to 10% by weight of polyol(s), with respect to the weight of the emulsion.

The emulsion of the invention exhibits the novel feature of being very fluid in comparison with the existing liquid products for making up the lips.

The viscosity of the emulsion at 25° C. and atmospheric pressure is preferably between 1000 and 10 000 mPa·s, more preferably between 1000 and 5000 mPa·s.

This viscosity can be measured with a RHEOLAB® QC (Anton Paar) viscometer having RHEOPLUS® software using a four-bladed spindle ST 22-4V (rotational speed 100 rev/min and measurement time 3 min).

Prior to the measurement, the emulsion of the invention is placed in a 120 ml jar (Ref: 102171001, KOLA ROND® VT3 M120 Blanc Pharm) in an oven at 25° C. for a minimum of 12 hours. Once the spindle is immersed in the jar, the level of composition has to reach the neck of the jar.

It is confirmed that the spindle is well chosen by measuring the percentage of deviation of the measurements, which are carried out every 6 seconds. The value of the viscosity of the emulsion is equal, according to this protocol, to the mean of the final fifteen measurements carried out by the appliance during the measurement time indicated above.

The emulsion of the invention can contain one or more molecules and/or one or more plant extracts exhibiting moisturizing properties, such as the glycols mentioned above, natural polyols, aloe vera, a sodium hyaluronate, a saccharide isomerate (Pentavitine®, for example) and any other moisturizing active principle known to a person skilled in the art.

Mention may be made, among inorganic pigments, by way of examples, of titanium dioxide, optionally surface-treated; black, yellow, red and brown iron oxides; and manganese violet.

Mention may be made, among inorganic pigments, by way of examples, of titanium dioxide; black, yellow, red and brown iron oxides; and manganese violet.

Mention may be made, among organic pigments, for example, of the pigments D&C Red No. 27; D&C Red No. 22; D&C Red No. 21; D&C Red No. 28; D&C Orange No. 4; D&C Red No. 33; D&C Red No. 7; D&C Red No. 6; D&C Yellow No. 5; D&C Red No. 36; D&C Yellow No. 6; D&C Red No. 30; D&C Blue 1 and lakes based on cochineal carmine.

Mention will be made, among dyes, of Yellow 5, Yellow 6, Blue 1, Green 5, Green 3, Green 6, Orange 4, Red 4, Red 21, Red 22, Red 27, Red 28, Red 33, Red 40 and cochineal carmine (CI 15850, CI 75470). Fat-soluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Pearlescent pigments can be chosen in particular from white pearlescent pigments, such as mica covered with titanium oxide or bismuth oxychloride; and colored pearlescent pigments, such as titanium oxide-coated mica with iron oxides or titanium oxide-coated mica with an organic pigment of the abovementioned type; and also pigments based on bismuth oxychloride. These pigments can have the following INCI names: CALCIUM SODIUM BOROSILICATE, TIN OXIDE, SYNTHETIC FLUORPHLOGOPITE, SILICA, ALUMINA, ALUMINUM HYDROXIDE, MICA and CALCIUM ALUMINUM BOROSILICATE.

The emulsion of the invention contains, for example, from 0.01% to 20% by weight of coloring material, with respect to the weight of the emulsion. The pearlescent agents can thus represent from 0% to 15% by weight, the organic and inorganic pigments from 0% to 3% and the dyes from 0.01% to 1% by weight of the weight of the emulsion.

Besides the ingredients described above, the emulsion of the invention comprises at least one cosmetically or dermatologically acceptable excipient which can be chosen from fragrances, electrolytes, sweeteners for masking the bitterness of some compounds of the emulsion when the latter is applied to the lips, pH adjusters and preservatives, sunscreens or also antioxidants.

The invention also relates to a method for caring for or making up the lips which consists in applying, to the lips, a product as described above. All the characteristics which were described in connection with these products apply to the method for making up of the invention.

The emulsion of the invention according to one of the aspects described above is a product for caring for or making up the lips which provides a very glossy rendering and which is not suited to other uses, such as caring for or making up the skin, for which the gloss is a totally unacceptable failing: this is the case in particular with the makeup or care products as an oil-in-water emulsion of lotion, serum, cream or foundation type.

The emulsion preferably comprises less than 1% by weight, preferably less than 0.5%, indeed even is devoid, of waxes, the melting point of which is greater than 70° C., as their crystallization creates mattness, which it is specifically wished to avoid.

The invention relates to a bottle, preferably a transparent bottle, having an application means containing the lip product described above. The product according to the invention is advantageously packaged in a transparent bottle (or pot) having an application means and a cap (or stopper). The application means can be a fine brush or a cellular foam and can advantageously be attached to the cap. The fine brush is preferably flat and its end can be straight or rounded. The bottle can have a cylindrical, cubic or parallelepipedal shape. The applicator can have different shapes—cylindrical, oblong or flat, for example—and optionally be bevelled in order to improve the accuracy of the application of the emulsion to the lips.

Finally, the invention relates to a process for the preparation of one of the emulsions described above.

A specific embodiment of this process comprises at least three stages. In a first stage, the ingredients of the fatty phase are mixed and a milled product of pigments which has been prepared beforehand is dispersed therein. In a second stage, all the ingredients of the aqueous phase are dissolved in water. Finally, in a third stage, the two phases, preheated to a temperature of the order of 70° C. to 80° C., are mixed.

Active principles and fragrances can be added at ambient temperature.

The invention is illustrated in more detail by the following examples.

Example 1: Invention

A liquid lipstick is prepared, the formula of which is presented in table 1. The percentages are by weight of the composition.

TABLE 1

| Phase | INCI name in upper case letters or function in lower case letters | % |
|---|---|---|
| A1 | METHYL HYDROGENATED ROSINATE | 10 |
| A1 | HYDROGENATED POLYISOBUTENE | 9 |
| A1 | HYDROGENATED POLYCYCLOPENTADIENE | 4 |
| A1 | BIS-BEHENYL/ISOSTEARYL/PHYTOSTERYL DIMER DILINOLEYL DIMER DILINOLEATE | 6 |
| A1 | CAPRYLIC/CAPRIC TRIGLYCERIDES | 4 |
| A1 | STEARETH-21 | 2.4 |
| A1 | MYRETH-3 MYRISTATE | 0.5 |
| A1 | STEARETH-2 | 0.5 |
| A2 | POLYGLYCERYL-2 TRIISOSTEARATE | 9.5 |
| A2 | Pigments | 3 |
| B1 | AQUA | q.s. for 100 |
| B1 | GLYCERIN | 5 |
| B1 | Preservatives | q.s. |
| B1 | Dyes | 0.12 |
| B2 | HYDROXYETHYL ACRYLATE/SODIUM ACRYLOYLDI METHYL TAURATE COPOLYMER | 0.7 |
| B2 | POLYSORBATE 60 | 0.1 |
| B2 | SORBITAN ISOSTEARATE | 0.03 |
| B2 | SQUALANE | 0.5 |
| B3 | Active principle | 1.6 |
| C | ALCOHOL | 3 |
| C | Fragrance | q.s. |

Preparation Process:

Phase A: A2 is dispersed in A1 for 5 min in a homogenizer of Turrax® brand at a stirring speed of 10 000 rev/min, and the phase A is heated to 75° C.

Phase B: the dyes are dissolved in the water with stirring with an emulsifying device of the trademark RAYNERI® brand for 20 min, and then the phase B is heated to 75° C. The phase B is subsequently emulsified in the phase A with an emulsifying device of the trademark RAYNERI® brand for 10 min at a stirring speed of 2000 rev/min, then cooling is allowed to take place while maintaining the stirring down to 40° C., in order to subsequently add the phases B2, B3 and then B4. This mixture is allowed to cool to 35° C. and then C is added.

Measurement of the Viscosity

The viscosity of the emulsion of example 1 according to the invention was measured with a viscometer sold under the trademark RHEOLAB® QC (by Anton Paar) having a software sold under the trademark RHEOPLUS®, with the vane spindle rotating at 50 rev/min for 3 minutes.

Prior to the measurement, the composition is poured into a 120 ml jar (Ref: 102171001, sold under the trademark KOLA ROND® VT3 M120 Blanc Pharm) and then the assembly is placed in an oven at 25° C. for a minimum of 12 hours. Once the spindle is immersed in the jar, the level of composition reaches the neck of the jar.

The value of the viscosity of the emulsion is equal to the mean of the final fifteen measurements carried out by the appliance during the measurement time indicated above.

Result: the viscosity of example 1 of the invention was equal to 2560 mPa·s.

Homogeneity

The emulsion prepared above and a commercial product in the form of a water-in-oil emulsion (Mintel Sheet No. 2401385) were observed with a microscope at a magnification of 200 microns.

Figure 2:
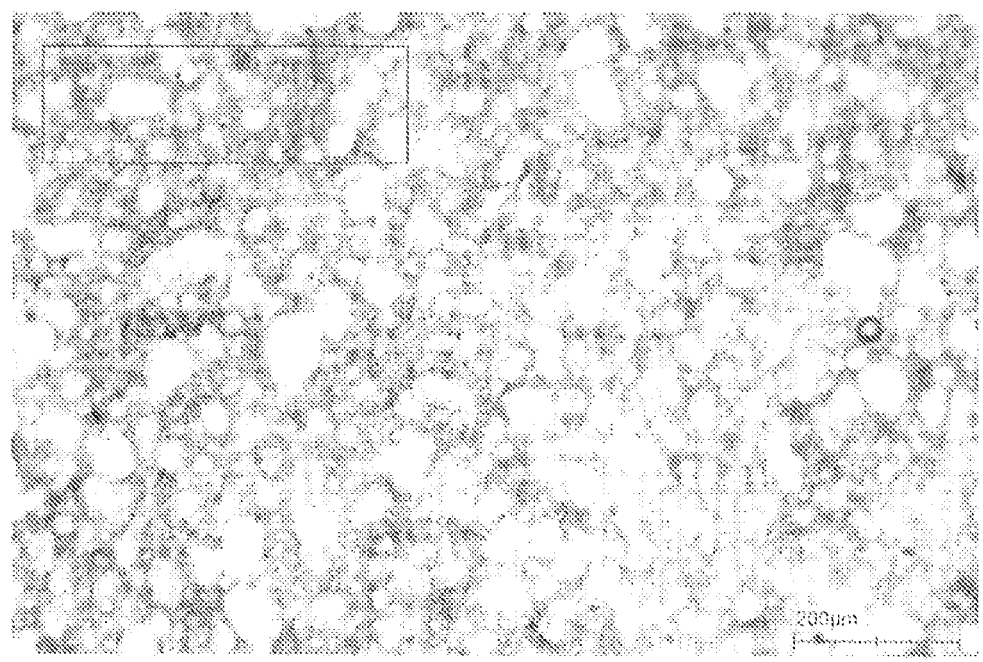

The microscope photographs for the product of the invention and the product of the prior art are presented in FIGS. 1 and 2 respectively.

Cutaneous Objectivation Study: Measurement of the Moisturizing Power

The moisturizing power of example 1 of the invention was measured by means of a corneometer sold under the trademark CM 825® (Courage and Khazaka) on 11 Caucasian volunteers, an application being carried out on the forearm (T=0).

Two skin zones of 25 centimeters squared are chosen according to a random distribution on the interior face of the forearm of each volunteer. The emulsion is applied to one of the two predetermined zones in a proportion of 2 mg/cm$^2$ of "in use" fashion; the second untreated zone acts as control.

The moisturizing effect of the emulsion at the time T=X hours is defined as being equal to the percentage of increase between the capacitance measured at the time T=X hours on an untreated skin zone of the forearm and the capacitance measured at the time T=X hours on the skin zone of the forearm to which the emulsion of example 1 according to the invention has been applied after withdrawal of the residual film.

The same protocol was followed for measuring the moisturizing power of a commercial product in the form of a water-in-oil emulsion (Mintel Sheet No. 2401385).

Results:

The emulsion of the invention exhibits a greater moisturizing power (+84% at T=16 hours and +78% at T=24 hours) than that of the product of the prior art (+16% at T=6 hours). This effect persists over time.

Evaluation of the Plumping Effect

The product of example 1 of the invention was evaluated on a panel of 20 female volunteers aged from 18 to 44 years (mean age of 35.0 years).

The product was applied just once to the lips and two observations are carried out:
  lips are photographed before and after application of the product,
  a dermatologist examines the lips before and after application of the product.

The image analysis made it possible to establish that the product of example 1 provides an immediate plumping effect. The mean of the percentage of variation in the area under the curve before and after application of the product was +25%. The mucocutaneous angle increased by 3% and the angle of curvature decreased by 9%.

The clinical evaluation confirmed it. The percentage of variation in the plumping effect determined by the dermatologist was +29% for the entire panel.

Sensory Analysis

A panel of 14 people trained for the sensory analysis of liquid lipsticks is formed.

Each member the panel assigns a grade ranging from 0 to 10 for each of the descriptors mentioned in table 2 below, and separately evaluates the lipstick of example 1 and the product of the prior art (Mintel Sheet No. 2401385, Color number 9). The coverage corresponds to the uniformity of the color after a single pass of the product.

The results which are significant (a less than or equal to 10%) are presented in table 2.

TABLE 2

| Descriptor | Grade out of 10 | |
| --- | --- | --- |
| | Example 1 | Liquid lipstick of the prior art |
| Coverage | 7.6 | 6.8 |
| Distinct outline | 7.6 | 7.0 |
| Film uniform in color and in thickness | 7.2 | 6.2 |
| Glossy film | 7.4 | 6.7 |
| Faithfulness of the color | 7.9 | 7.6 |
| Lacquered effect of very uniform gloss | 6.1 | 5.7 |
| Full lips | 7.1 | 6.5 |

Self-Evaluations

The product of example 1 of the invention was evaluated by a panel of 32 female volunteers of Caucasian type aged from 20 to 65 years (mean age of 46.0 years) who were not trained for the evaluation of cosmetic products. Each woman applies the product to the lips twice daily for four consecutive weeks.

Each woman of the panel evaluated herself the effects and the properties of the product by answering a questionnaire on conclusion of the test period. The volunteers answered a questionnaire by recording: "agree", "somewhat agree", "somewhat disagree" and "completely disagree". For each item, the percentage of satisfaction (number of "agree" and "somewhat agree" replies) is calculated.

The results obtained which were statistically significant are given in table 3 below.

TABLE 3

| Property evaluated | Percentage of satisfaction |
| --- | --- |
| The texture is fresh, light and extra-fine | 84 |
| The product leaves a thin and light film on the lips | 81 |
| The product leaves a non-greasy and non-tacky film | 84 |
| The gloss is lacquered | 94 |
| A smoothing glossy film is formed above the color | 88 |
| The coverage is satisfactory | 84 |
| The lips are smoothed | 91 |

The inexperienced consumers judged the makeup result obtained with the emulsion of example 1 according to the invention to be very glossy and light. The film smooths the lips so much so that the level of gloss reaches that of a lacquer.

The consumers recorded qualities identical to those which were demonstrated by the panel of people trained for the evaluation of liquid lipsticks, which confirms the significativity of the results.

Example 2: Comparative

A composition not in accordance with the invention, the list of the ingredients of which is reproduced in table 4, was prepared.

This composition contains 29.2% of a mixture of water and of glycerol, 48.5% of a mixture of glossy oils, 3.1% of coloring material and two stearyl alcohol ethers (STEARETH-2 and STEARETH-21). It is devoid of the copolymer of acrylamido-2-methylpropanesulfonate and of hydroxyethyl acrylate, which has been replaced by a xanthan gum.

TABLE 4

| Phase | INCI name in upper case letters or chemical name in lower case letters | % |
|---|---|---|
| A1 | PHENYLPROPYLDIMETHYLSILOXYSILICATE | 23 |
| A1 | HYDROGENATED POLYISOBUTENE | 9 |
| A1 | HYDROGENATED POLYCYCLOPENTADIENE | 4 |
| A1 | BIS-BEHENYL/ISOSTEARYL/PHYTOSTERYL DIMER DILINOLEYL DIMER DILINOLEATE | 4 |
| A1 | CAPRYLIC/CAPRIC TRIGLYCERIDES | 4 |
| A1 | STEARETH-21 | 2.2 |
| A1 | MYRETH-3 MYRISTATE | 2 |
| A1 | STEARETH-2 | 0.7 |
| A2 | POLYGLYCERYL-2 TRIISOSTEARATE | 9.5 |
| A2 | Pigments | 3 |
| B1 | AQUA | q.s. for 100 |
| B1 | GLYCERIN | 5 |
| B1 | Preservatives | 0.9 |
| B1 | Dyes | 0.1 |
| B2 | XANTHAN GUM | 0.4 |
| B3 | Active principles | 1.6 |
| C | ALCOHOL | 3.4 |
| C | Fragrance | 3 |

The emulsion is prepared according to the process of example 1. It is unstable: a sedimentation of the pigments and a phase separation between the aqueous phase and the fatty phase are observed.

Example 3, Comparative

A composition not in accordance with the invention, the list of the ingredients of which is reproduced in table 5, was prepared.

This composition contains a mixture of water and of glycerol, 35.5% of a mixture of glossy oils and coloring materials. The two stearyl alcohol ethers (STEARETH-2 and STEARETH-21) present in example 1 have been replaced with GLYCERYL STEARATE SE and SODIUM STEAROYL GLUTAMATE. It is also devoid of the copolymer of acrylamido-2-methylpropanesulfonate and of hydroxyethyl acrylate, which has been replaced by a xanthan gum.

TABLE 5

| Phase | INCI name in upper case letters or function in lower case letters | % |
|---|---|---|
| A1 | METHYL HYDROGENATED ROSINATE | 10 |
| A1 | HYDROGENATED POLYISOBUTENE | 9 |
| A1 | HYDROGENATED POLYCYCLOPENTADIENE | 4 |
| A1 | BIS-BEHENYL/ISOSTEARYL/PHYTOSTERYL DIMER DILINOLEYL DIMER DILINOLEATE | 3 |
| A1 | CAPRYLIC/CAPRIC TRIGLYCERIDES | 4 |
| A1 | GLYCERYL STEARATE SE | 5 |
| A1 | SODIUM STEAROYL GLUTAMATE | 2 |
| A2 | POLYGLYCERYL-2 TRIISOSTEARATE | 9.5 |
| A2 | Pigments | 3 |
| B1 | AQUA | q.s. for 100 |
| B1 | GLYCERIN | 5 |
| B1 | Preservatives | q.s. |
| B1 | Dyes | 0.1 |
| B2 | XANTHAN GUM | 0.4 |
| B3 | Active principles | 1.6 |
| C | ALCOHOL | 3 |
| C | Fragrance | q.s. |

The emulsion is prepared according to the process of example 1. It is unstable: a sedimentation of the pigments and a phase separation between the aqueous phase and the fatty phase are observed.

The invention claimed is:

1. A liquid product for making up and caring for the lips as an oil-in-water emulsion comprising:
   from 25% by weight to 45% by weight of a mixture of water and of at least one polyol,
   from 35% by weight to 60% by weight of a mixture of oils, each having a refractive index, measured at a temperature ranging from 20° C. to 25° C., which is greater than or equal to 1.460,
   from 0.01% by weight to 20% by weight of a coloring material,
   the percentages being expressed with respect to the weight of the product,
   wherein the liquid product comprises a first polyethylene glycol ether of stearyl alcohol comprising from 2 to 5 oxyethylene units, a second polyethylene glycol ether of stearyl alcohol comprising from 15 to 25 oxyethylene units, and an acrylamido-2-methylpropane sulfonate copolymer.

2. The product as claimed in claim 1, wherein the mixture of oils comprises methyl hydrogenated rosinate and hydrogenated polycyclopentadiene.

3. The product as claimed in claim 2, wherein the methyl hydrogenated rosinate represents between 10% by weight and 15% by weight of the weight of the product.

4. The product as claimed in claim 2, wherein the hydrogenated polycyclopentadiene represents between 2% by weight and 5% by weight of the weight of the product.

5. The product as claimed in claim 1, wherein the first polyethylene glycol ether of stearyl alcohol is part of a component having the INCI name STEARETH-2 and wherein the second polyethylene glycol ether of stearyl alcohol is part of a component having the INCI name STEARETH-21.

6. The product as claimed in claim 1, wherein the acrylamido-2-methylpropane sulfonate copolymer is a copolymer of acrylamido-2-methylpropane sulfonate and of hydroxyethyl acrylate, and represents between 0.2% by weight and 1.0% by weight of the weight of the product.

7. A process for making up and caring for the lips and comprising applying to the lips the product as claimed in claim 1.

8. A bottle having an applicator and a cap, wherein the bottle is transparent and contains the product as claimed in claim 1, said applicator being a fine brush or a cellular foam.

* * * * *